(12) United States Patent
Lee et al.

(10) Patent No.: US 9,448,181 B2
(45) Date of Patent: Sep. 20, 2016

(54) OPTICAL BIOSENSOR AND BIOSENSING SYSTEM WITH RESONANT FEEDBACK CONTROLS

(71) Applicant: SAMSUNG ELECTRONICS CO., LTD., Suwon-si, Gyeonggi-do (KR)

(72) Inventors: Kwang-hyun Lee, Hwaseong-si (KR); Seok-yong Hong, Seoul (KR)

(73) Assignee: SAMSUNG ELECTRONICS CO., LTD., Suwon-Si, Gyeonggi-Do (KR)

( * ) Notice: Subject to any disclaimer, the term of this patent is extended or adjusted under 35 U.S.C. 154(b) by 182 days.

(21) Appl. No.: 14/192,926

(22) Filed: Feb. 28, 2014

(65) Prior Publication Data
US 2014/0263948 A1 Sep. 18, 2014

(30) Foreign Application Priority Data

Mar. 14, 2013 (KR) .................. 10-2013-0027496

(51) Int. Cl.
*G01N 21/77* (2006.01)
*G01N 1/00* (2006.01)

(52) U.S. Cl.
CPC ............. *G01N 21/7746* (2013.01); *G01N 1/00* (2013.01)

(58) Field of Classification Search
CPC ...................... G01N 1/00; G01N 21/7746
See application file for complete search history.

(56) References Cited

U.S. PATENT DOCUMENTS

| 7,257,279 | B2 | 8/2007 | Guo et al. |
| 7,260,279 | B2 | 8/2007 | Gunn et al. |
| 7,385,177 | B2 | 6/2008 | Steinberg et al. |
| 7,595,890 | B2 | 9/2009 | Fan et al. |
| 7,693,369 | B2 | 4/2010 | Fan et al. |
| 7,729,572 | B1 | 6/2010 | Pepper et al. |
| 7,840,101 | B2 | 11/2010 | Wong et al. |
| 7,885,490 | B2 | 2/2011 | Heideman et al. |
| 7,933,022 | B2 | 4/2011 | Smith et al. |
| 8,142,723 | B2 | 3/2012 | Menon et al. |
| 2007/0197885 | A1* | 8/2007 | Mah .................. A61B 5/14532 600/310 |
| 2012/0064519 | A1 | 3/2012 | Fang et al. |

FOREIGN PATENT DOCUMENTS

| KR | 1020100130479 | 12/2010 |
| KR | 1020110082939 | 7/2011 |
| KR | 1020120042458 | 5/2012 |

* cited by examiner

*Primary Examiner* — Francis M Legasse, Jr.
(74) *Attorney, Agent, or Firm* — F. Chau & Associates, LLC

(57) ABSTRACT

An optical biosensor is provided. The optical biosensor includes a biosensing unit, a detection unit, and a feedback circuit. The biosensing unit is configured to receive an input optical signal, sense a biomaterial, and generate a sensed optical signal. The detecting unit is configured to convert the sensed optical signal into an electrical signal and output the electrical signal as a detection signal. The feedback circuit is configured to output a feedback signal. The feedback signal is generated based on the detection signal and is changed according to a changed amount of a resonant wavelength of the biosensing unit.

17 Claims, 11 Drawing Sheets

OPTICAL BIOSENSOR AND BIOSENSING SYSTEM WITH RESONANT FEEDBACK CONTROLS

CROSS-REFERENCE TO RELATED APPLICATIONS

This application claims priority under 35 U.S.C. §119 to Korean Patent Application No. 10-2013-0027496, filed on Mar. 14, 2013, in the Korean Intellectual Property Office, the disclosure of which is incorporated by reference in its entirety herein.

TECHNICAL FIELD

The inventive concept relates to an optical biosensor and a biosensing system, and more particularly, to an integrated optical biosensor and a biosensing system based on a silicon photonics technology.

DISCUSSION OF THE RELATED ART

A biosensor may measure concentration of an organic material or an inorganic material in a liquid or gas state. The biosensor may include a piezoelectric-based biosensor, an optical biosensor, an electrochemical biosensor, or the like. The optical biosensor may measure optically concentration of a biomaterial by allowing a biological element in the biomaterial to interact with another biomaterial. The optical biosensor may sense change of a resonant wavelength in a biosensing unit varying according to biomolecules. The sensed changed amount of the resonant wavelength may be used to determine an amount of the target biomaterial.

SUMMARY

According to an embodiment of the present inventive concept, an optical biosensor is provided. The optical biosensor a biosensing unit, a detecting unit, and a feedback circuit. The biosensing unit is configured to receive an input optical signal, sense a target biomaterial, and generate a sensed optical signal. The detecting unit is configured to convert the sensed optical signal into an electrical signal and output the electrical signal as a detection signal. The feedback circuit is configured to output a feedback signal. The feedback signal is generated based on the detection signal and is changed according to changed amount of a resonant wavelength of the biosensing unit.

In an embodiment of the inventive concept, the feedback circuit may control the resonant wavelength of the biosensing unit to be equal to the wavelength of the input optical signal by using the feedback signal.

In an embodiment of the inventive concept, the feedback circuit may control the wavelength of the input optical signal to be equal to the wavelength of the resonant wavelength of the biosensing unit by using the feedback signal.

In an embodiment of the inventive concept, the feedback signal may be a voltage or current signal.

In an embodiment of the inventive concept, the biosensing unit may include a resonator and a phase shifter. The resonator may be configured to provide the resonant wavelength and to output the sensed optical signal. The phase shifter may be configured to receive the feedback signal and change the resonant wavelength of the resonator in response to the feedback signal.

In an embodiment of the inventive concept, the biosensing unit may include an optical waveguide, a ring resonator, and a phase shifter. The optical waveguide may be configured to receive the input optical signal. The ring resonator may be configured to provide the resonant wavelength and to output the sensed optical signal through a gap interposed between the optical waveguide and the ring resonator. The phase shifter may be configured to change the resonant wavelength of the ring resonator in response to the feedback signal.

In an embodiment of the inventive concept, the biosensing unit may include a first optical waveguide, a ring resonator, a phase shifter, a second optical waveguide. The first optical waveguide may be configured to receive the input optical signal. The ring resonator may be to provide the resonant wavelength and to output the sensed optical signal through a gap interposed between the first optical waveguide and the ring resonator. The phase shifter may be configured to change the resonant wavelength in response to the feedback signal. The second optical waveguide may be configured to receive the sensed optical signal through a gap interposed between the ring resonator and the second optical waveguide.

In an embodiment of the inventive concept, the biosensing unit may include a first optical waveguide, a cavity resonator, a second optical waveguide, and a phase shifter. The first optical waveguide may be configured to receive the input optical signal. The cavity resonator may be configured to provide the resonant wavelength and to output the sensed optical signal. The second optical waveguide may be configured to receive and output the sensed optical signal. The phase shifter may be configured to change the resonant wavelength of the cavity resonator.

In an embodiment of the inventive concept, the cavity resonator may include a Bragg reflector.

The optical biosensor may further include an optical source providing the input optical signal.

The optical source may be configured to change the wavelength of the input optical signal in response to the feedback signal.

The feedback signal may be a voltage or current signal for controlling the optical source to adjust the wavelength of the input optical signal to be equal to the resonant wavelength.

In an embodiment of the inventive concept, the optical source, the biosensing unit, the detecting unit, and the feedback circuit may be formed on the same substrate.

In an embodiment of the inventive concept, the optical biosensor may further include a signal processing unit calculating the concentration of the target biomaterial by calculating difference between a reference feedback signal generated when the probe biomaterial is attached to the biosensing unit and a sensing feedback signal generated when the target biomaterial is combined into the probe biomaterial.

According to an embodiment of the present inventive concept, a biosensing system is provided. The biosensing system includes a biosensor chip and a signal processing unit. The biosensor chip is configured to sense a target biomaterial based on an input optical signal and output a feedback signal. The signal processing unit is configured to analyze the feedback signal and calculate the concentration of the target biomaterial. The biosensor chip includes a biosensing unit, a detecting unit, and a feedback unit. The biosensing unit may be configured to receive the input optical signal, sense the target biomaterial, and generate a sensed optical signal. The detecting unit may be configured to convert the sensed optical signal into an electrical signal and output the electrical signal as a detection signal. The feedback circuit may be configured to output the feedback signal generated based on the detection signal.

In an embodiment of the inventive concept, the feedback circuit may control the resonant wavelength of the biosensing unit to be equal to the wavelength of the input optical signal by using the feedback signal.

In an embodiment of the inventive concept, the feedback circuit may control the wavelength of the input optical signal to be equal to the resonant wavelength of the biosensing unit by using the feedback signal.

In an embodiment of the inventive concept, the biosensing unit may include a resonator. The resonator may be configured to provide the resonant wavelength and to output the sensed optical signal. The signal processing unit may calculate the concentration of the target biomaterial by calculating difference between a feedback signal generated when a probe biomaterial is attached to the biosensing unit and a feedback signal generated when the target biomaterial is combined into the probe biomaterial.

In an embodiment of the inventive concept, the biosensing system may further include an optical source generating the input optical signal. The optical source may be integrated on a substrate which the biosensor chip is formed.

According to an embodiment of the present inventive concept, a biosensing method is provided. The biosensing method includes measuring a reference feedback signal generated when a probe biomaterial is attached to a resonator, measuring a sensing feedback signal generated when a target biomaterial is combined into the probe biomaterial, calculating changed amount of a resonant wavelength in the resonator based on the difference between the reference feedback signal and the sensing feedback signal, and calculating the concentration of the target biomaterial from the changed amount of the resonant wavelength.

In an embodiment of the inventive concept, the biosensing method may further include storing a data about the changed amount of the resonant wavelength according to the concentration of the target biomaterial.

BRIEF DESCRIPTION OF THE DRAWINGS

Exemplary embodiments of the inventive concept will be more clearly understood from the following detailed description taken in conjunction with the accompanying drawings in which:

FIG. 4A is a cross-sectional view when a target biomaterial is DNA. FIG. 4B is a cross-sectional view when a target biomaterial is an anti-body;

FIG. 5A illustrates an optical biosensor when a probe biomaterial (e.g. Ab) is attached to a surface of a ring resonator. FIG. 5B illustrates an optical spectral transmittance of the ring resonator of FIG. 5A (see, for example, short dotted line). FIG. 5C illustrates the optical biosensor when a target biomaterial (e.g. Ag) is combined into the probe biomaterial of FIG. 5A. FIG. 5D illustrates an optical spectral transmittance of the ring resonator of FIG. 5C (see, for example, long dotted line).

FIG. 10A illustrates an optical biosensor when a probe biomaterial (e.g. Ab) is attached to a surface of a ring resonator. FIG. 10B illustrates an optical spectral transmittance of the ring resonator of FIG. 10A. FIG. 10C illustrates the optical biosensor when a target biomaterial (e.g. Ag) is combined into the probe biomaterial of FIG. 10C. FIG. 10D illustrates an optical spectral transmittance of the ring resonator of FIG. 10C;

DETAILED DESCRIPTION OF THE EMBODIMENTS

The present inventive concept will be described with reference to the accompanying drawings. The present inventive concept may be embodied in different forms and should not be construed as limited to the embodiments set forth herein. In the accompanying drawings, thickness of layers, sizes of structures may be exaggerated for clarity.

As used herein, the singular forms "a," "an" and "the" are intended to include the plural forms, unless the context clearly indicates otherwise.

Figure 1:
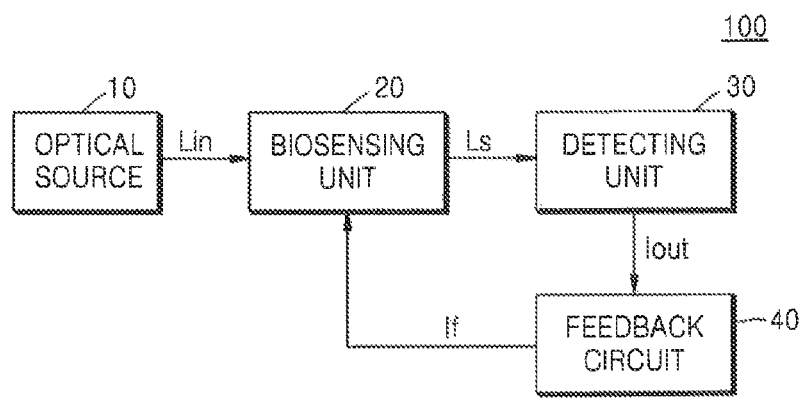
FIG. 1 is a block diagram illustrating an optical biosensor according to an embodiment of the present inventive concept.
Figure 2:
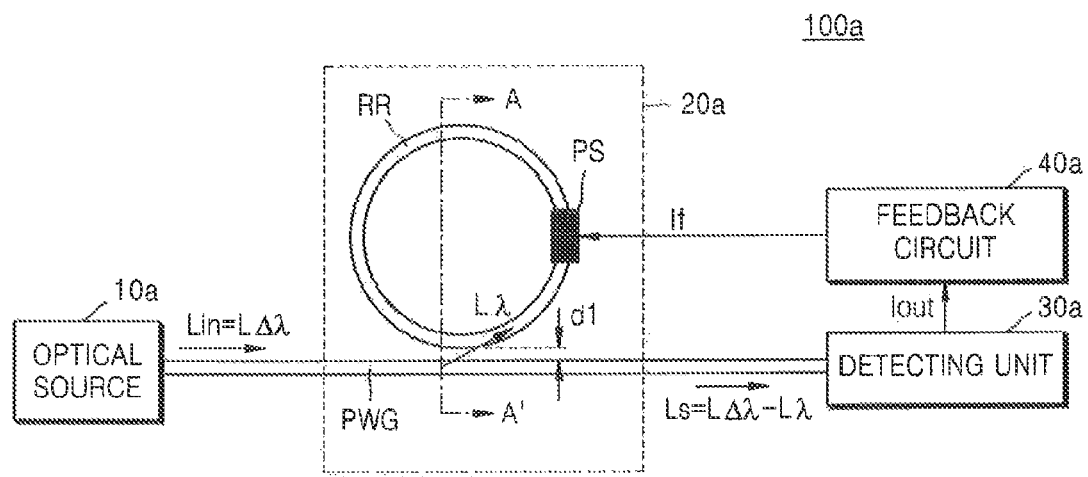
FIG. 2 illustrates an example of the optical biosensor of FIG. 1.

FIG. 1 is a block diagram illustrating an optical biosensor according to an embodiment of the present inventive concept. FIG. 2 illustrates an example of the optical biosensor of FIG. 1.

Referring to FIG. 1, the optical biosensor 100 may include a biosensing unit 20, a detecting unit 30, and a feedback circuit 40. The optical biosensor may further include an optical source 10. Referring to FIG. 2, the optical biosensor 100a may include an optical source 10a, a biosensing unit 20a, a detecting unit 30a, and a feedback circuit 40a. Hereinafter, elements of the optical biosensor 100a are described.

The optical biosensor 100 may determine the concentration of a biomaterial (refer to as 'a target biomaterial') based on an interaction of the target biomaterial with another biomaterial (refer to as 'a probe biomaterial'). The interaction between the probe biomaterial and the target biomaterial may be an optical phenomenon generated according to a combination of a target biomaterial (for example, a target DNA or an antigen) and a probe biomaterial (for example, a probe DNA or an antibody).

The optical source 10 may generate an input light signal Lin. The generated input light signal Lin may be transmitted to the biosensing unit 20. The biosensing unit 20 may receive the input optical signal Lin and generate a sensed optical signal Ls. The sensed optical signal Ls may be a signal whose resonant wavelength component is extracted from the input optical signal. The sensed optical signal Ls may be a signal whose resonant wavelength component is dropped from the input optical signal Lin. The resonant wavelength may be changed according to the concentration of the biomaterial attached to the biosensing unit 20.

The detecting unit 30 may receive the sensed optical signal Ls, convert the sensed optical signal Ls into an electrical signal, and output the electrical signal as a detection signal Iout. The detection signal Iout may be a voltage signal or a current signal.

The feedback circuit 40 may output a feedback signal If. The feedback signal may be transmitted to the biosensing unit 20 and control a resonant wavelength of the biosensing unit 20 to be changed. The feedback signal If may be a voltage signal or a current signal.

The resonant wavelength of the biosensing unit 20 may be controlled by the feedback signal If, to be the same as the input optical signal Lin. The feedback circuit 40 may monitor change in the detection signal Iout and finally, output the feedback signal If. The feedback signal If may control the strength of the detection signal Iout to be a minimum or a maximum. For example, when the sensed optical signal Ls is an optical signal whose resonant wavelength component is dropped from the input optical signal Lin, the strength of the detection signal Iout may be a maximum when the resonant wavelength and the wavelength of the input optical signal Lin are equal. For example, when the sensed optical signal Ls is an optical signal whose resonant wavelength component is extracted from the input optical signal Lin, the strength of the detection signal Iout when the resonant wavelength and the wavelength of the input optical signal Lin are equal may be a maximum. The feedback signal If generated based on the detection signal Iout may be output to control the resonant wavelength to be the same as the wavelength of the input optical signal Lin.

The optical biosensor 100 may measure the feedback signal If to analyze the changed amount of the resonant wavelength. A resonant wavelength of the biosensing unit 20 may be maintained to be the same as the wavelength of the input optical signal Lin due to a feedback signal generated from the feedback circuit 40. The feedback signal If may be changed as the resonant wavelength is changed. The resonant wavelength may be changed due to the change in the concentration of the biomaterial attached to the biosensing unit. A detailed operation of the optical biosensor 100 and a method of calculating concentration of the biomaterial will be described with reference to FIGS. 2 to 5D.

In an embodiment of the inventive concept, the biosensing unit 20, the detecting unit 30, and the feedback circuit 40 may be formed or packaged on the same substrate. In an embodiment of the inventive concept, the optical source 10, the biosensing unit 20, the detecting unit 30, and the feedback circuit 40 may be formed or packaged on the same substrate. However, other combinations of optical source 10, the biosensing unit 20, the detecting unit 30, and the feedback circuit 40 may be formed or packaged on the same substrate.

Since an optical biosensor may determine concentration of a biomaterial by analyzing wavelength of an optical signal used for a sensed biomaterial by using optical characteristics, a device such as a spectrometer may be necessary for analyzing the wavelength. According to an embodiment of the present inventive concept, the optical biosensor 100 does not directly analyze wavelength of a sensed optical signal used for the biomaterial, however the optical biosensor 100 may analyze changed amount of a resonant wavelength based on a feedback signal. The feedback signal may control a resonant wavelength of the optical biosensing unit 20 to be the same as the wavelength of the input optical signal. The optical biosensor 100 may measure a reference feedback signal when a probe biomaterial is attached to the biosensing unit 20 and a sensing feedback signal when a target biomaterial is combined into the probe biomaterial. The changed amount of the resonant wavelength may be calculated based on the difference between the reference feedback signal and the sensing feedback signal. The concentration of the target biomaterial may be calculated by the changed amount of the resonant wavelength.

FIG. 2 illustrates an example of the optical biosensor 100a of FIG. 1.

Referring FIG. 2, the optical biosensor 100a may include an optical source 10a, a biosensing unit 20a, a detecting unit 30a, and a feedback circuit 40a.

The optical source 10a may generate an input light signal Lin and transmit the input optical signal Lin to the biosensing unit 20a. The input optical signal Lin may include a wavelength component in a predetermined range with a central wavelength. In an embodiment, the optical source 10a may be an amplified spontaneous emission (ASE), a super luminescent light emitting diode (LED), a wavelength variable optical source such as a distributed feedback laser diode (DFD), or the like. The optical source 10a may include a wavelength adjustor (not shown). However, the optical source 10a is not limited thereto.

The biosensing unit 20a may generate a sensed optical signal Ls from the input optical signal Lin.

The biosensing unit 20a may include an optical waveguide PWG, a ring resonator RR, and a phase shifter PS disposed as a part of the ring resonator RR. Although not shown in the drawings, a fluidic channel is disposed on a top portion of the optical waveguide PWG and the ring resonator RR. The fluidic channel may become a passage into which the biomaterial flows.

The optical waveguide PWG may be a passage through which the input optical signals Lin and the sensed optical signal Ls are passed. The biosensing unit 20a may receive the input optical signal Lin and output the sensed optical signal Ls.

The ring resonator RR may be positioned with a predetermined gap interposed from the optical waveguide PWG. The ring resonator RR may be an optical waveguide having a circular or racetrack form. A resonant wavelength of the ring resonator RR may be changed as the concentration of the biomaterial attached to the ring resonator RR is changed. The ring resonator RR may generate a sensed optical signal Ls by dropping the resonant wavelength $\lambda r$ from the input optical signal Lin. The ring resonator RR may generate a sensed optical signal Ls by extracting the resonant wavelength $\lambda r$ from the input optical signal Lin. The sensed optical signal Ls may be provided to the optical waveguide PWG. The detailed description about the optical waveguide PWG and the ring resonator RR will be described below with reference to FIGS. 3A to 4B.

The phase shifter PS may be disposed on a part of the ring resonator RR. The phase shifter PS may change the resonate wavelength of the ring resonator RR in response to an electrical signal applied to the phase shifter PS. For example, the resonant wavelength $\lambda r$ of the ring resonator RR may be changed by changing a refractive index in the resonator. The refractive index may be changed by the electrical signal. The electrical signal may be, for example, a current signal or a voltage signal.

The detecting unit 30a may receive the sensed optical signal Ls, convert the sensed optical signal Ls into an electrical signal, and output as a detection signal Iout. The detecting unit 30a may include one or more optical detectors in order to convert the sensed optical signal Ls to an electrical signal. For example, the optical detector may include a photodiode, a phototransistor, a charge coupled device (CCD) image sensor, a CMOS image sensor, a time of flight (TOF) sensor, or the like. However, the optical detector is not limited thereto.

The feedback circuit 40a may receive the detection signal Iout and output a feedback signal If generated based on the received detection signal Iout. The feedback signal If may be applied to the phase shifter PS of the biosensing unit 20 and change a resonant wavelength of the ring resonator RR. The feedback signal If may control the resonant wavelength of ring resonator RR to be the same as the wavelength of the input optical signal Lin. The feedback circuit 40a may change and output a feedback signal If until the strength of the detection signal Iout becomes a minimum. The strength of the detection signal Iout may be a minimum when the ring resonator RR generates a sensed optical signal Ls by dropping the resonant wavelength from the input optical signal Lin. The feedback circuit 40a may change and output a feedback signal If until the strength of the detection signal Iout becomes a maximum. The strength of the diction signal Iout may be a maximum when the ring resonator RR generates a sensed optical signal Ls by extracting the resonant wavelength from the input optical signal Lin.

When an input optical signal Lin having a predetermined bandwidth Δλ and a center wavelength λi is incident to the optical waveguide PWG, the input optical signal Lin may travel along the optical waveguide PWG and transit to the ring resonator RR through the predetermined gap d1 between the optical waveguide PWG and the ring resonator RR. A sensed optical signal Ls may be output through the optical waveguide PWG.

The sensed optical signal Ls may be transmitted to the detecting unit 30a and output as the detection signal Iout, which may be an electrical signal. The feedback circuit 40a may output the feedback signal If based on the detection signal Iout. The feedback signal If may be applied to the phase shifter PS and change the resonant wavelength λr of the ring resonator RR to be the same as the wavelength λi of the input optical signal Lin.

Figure 3A:
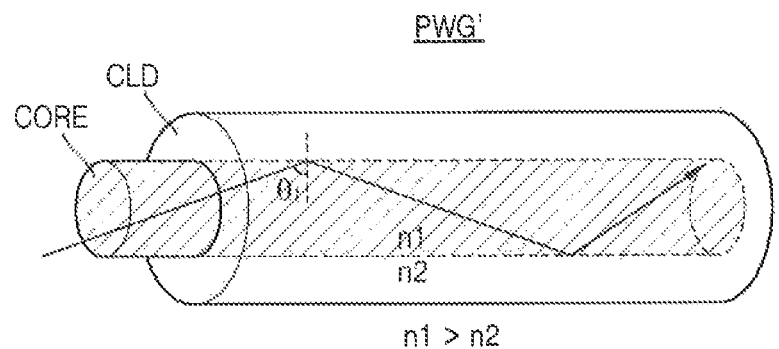
FIGS. 3A and 3B illustrate an example of the optical waveguides of FIG. 2.
Figure 3B:
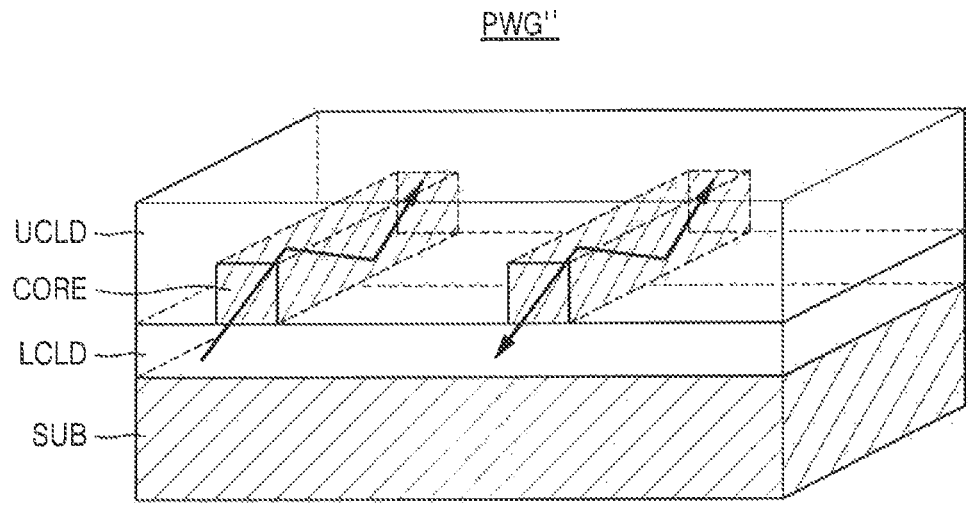

FIGS. 3A and 3B illustrate an example optical waveguides PWG' and PWG" which are included in the biosensing unit 20a in FIG. 2.

The optical biosensor 100 may be formed on a semiconductor substrate based on a silicon photonics technology. The biosensing unit 20a may include optical waveguides for transmitting the optical signals Lin and Ls. The optical waveguides may be formed on a semiconductor substrate.

Referring to FIG. 3A, the optical waveguide PWG' may include a core CORE through which an optical signal propagates and a cladding CLD enclosing the core CORE. The refractive index n1 of the core CORE is higher than a refractive index n2 of the cladding CLD. When an optical signal is incident with an angle θt greater than a threshold value, the optical signal may travel along the core CORE without being radiated to outside of the optical waveguide, due to total internal reflection.

Referring to FIG. 3B, the optical waveguide PWG" may be implanted into silicon waveguides formed on the semiconductor substrate SUB. A lower cladding layer LCLD may be formed on the semiconductor substrate SUB. A core layer CORE may be formed on the lower cladding layer LCLD. An upper cladding layer UCLD may be formed to enclose the core layer CORE. However, configuration of the optical waveguide PWG" is not limited thereto.

The core layer CORE may include silicon (Si) or a silicon-based composite (for example, silicon-nitride (SiN)). The lower cladding layer LCLD and the upper cladding layer UCLD may include an oxide (Ox). Since refractive indices of silicon and oxide are substantially 3.5 and 1.4, respectively, the refractive index of the core layer CORE is higher than that of the cladding layers LCLD and UCLD. When the optical signal is incident to the core layer CORE with an incident angle greater than a threshold angle, the optical signal may propagate along the core layer CORE, due to total internal reflection occurring on boundaries between the core layer CORE and the cladding layers LCLD, or the core layer COR and the cladding layers UCLD.

As an example, when the upper cladding layer UCLD may be a passivation layer. The upper cladding layer UCLD may be formed from silicon nitride (SiN) or polyimide (Pi). The refractive index of Silicon nitride (SiN) may be substantially 2.0. The refractive index of polyimide (Pi) may be substantially 1.7 lower than that of the core layer CORE and may meet an optical waveguide condition.

However, biomaterials used for forming the optical waveguides are not limited thereto.

Figure 4A:
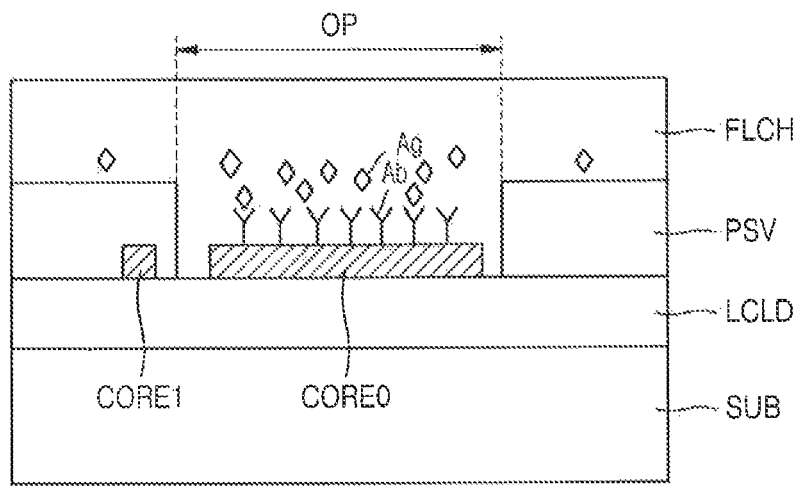
FIGS. 4A and 4B are cross-sectional views taken along a line A-A' in FIG. 2.
Figure 4B:
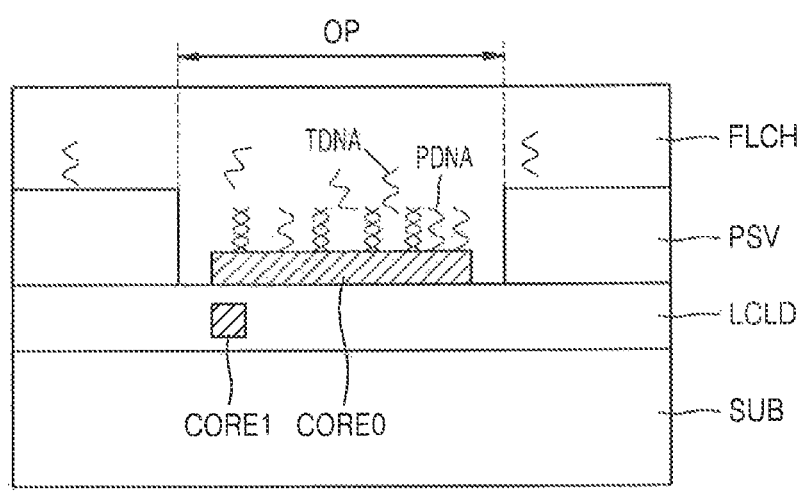

FIGS. 4A and 4B are cross-sectional views taken along a line A-A' of FIG. 2. FIG. 4A is a cross-sectional view when a target biomaterial is a DNA. FIG. 4B is a cross-sectional view when a target biomaterial is an antigen.

Referring to FIG. 4A, a core layer CORE1 of an optical waveguide PWG and a core layer CORE0 of a ring resonator RR may be formed on the same layer and disposed horizontally, for example on the same layer. The ring resonator RR may be disposed apart from the optical waveguide PWG with a predetermined interval interposed between the ring resonator RR and the optical waveguide horizontally, for example on a common layer. A passivation layer (PSV) may be formed on a top surface of the optical waveguide PWG. However, in order to have the ring resonator RR combined easily with a probe biomaterial, a passivation layer might not be formed on the top surface of the ring resonator RR. The top surface of the optical waveguide PWG may be remained open (see, for example, OP in FIGS. 4A and 4B or may be formed with a thin passivation layer.

Referring to FIG. 4B, the core layer CORE of the optical waveguides PWG may be formed on a layer lower than the core layer CORE0 (for example, inside the lower cladding layer LCLD). The core layer CORE0 of the ring resonator RR may be formed on a layer upper than the core layer CORE1 (for example, on a top surface of the lower cladding layer LCLD). The core layer CORE1 of the optical waveguide PWG and the core layer CORE0 of the ring resonator RR may be formed on different layers and disposed vertically. The ring resonator RR may be disposed apart from the optical waveguide PWG with a predetermined interval interposed between the ring resonator RR and the optical waveguide vertically.

Referring to FIGS. 4A and 4B, a probe biomaterial is attached on a surface of the core layer CORE0 of the ring resonator RR. The probe biomaterial may be attached on a surface of the core layer CORE0 of the ring resonator RR in a biological or physicochemical scheme. For example, in FIG. 4A, a target biomaterial may be an antigen Ag and a probe biomaterial may be an antibody Ab. For example, in FIG. 4B, a target biomaterial may be a target DNA TDNA, and a probe biomaterial may be a probe DNA PDNA.

For example, when the target biomaterial Ag or TDNA is combined into the probe biomaterial Ab or PDNA, an effective refractive index of the core CORE0 of the ring resonator RR may be changed. The resonant wavelength λr of the ring resonator RR may be changed as the effective refractive index of the core CORE0 is changed. The resonant wavelength λr of the ring resonator RR may be expressed as Equation 1;

$$\lambda_r = n_{eff} 2\pi R/m \quad (1)$$

where $n_{eff}$ denotes an effective refractive index, R denotes a radius of the ring resonator RR, and m denotes an integer.

Referring to equation 1, the resonant wavelength λr is proportional to the effective refractive index $n_{eff}$. Therefore, when the effective refractive index $n_{eff}$ is increased or decreased, the resonant wavelength λr of the ring resonator RR may be increased or decreased proportionally.

For example, when the probe biomaterial Ab or PDNA is attached to the ring resonator RR, the effective refractive index $n_{eff}$ may be n0 and the resonant wavelength λr may be λ0. When the target biomaterial Ag or TDNA is combined into the probe biomaterial Ab or PDNA, the effective refractive index of the ring resonator RR may be increased and the resonant wavelength λr may be increased. The changed amount of the effective refractive index of the ring resonator RR and the resonant wavelength λr may be determined by a combination degree between the probe biomaterial Ab or PDNA and the target biomaterial Ag or TDNA. The combination degree between the probe biomaterial Ab or PDNA and the target biomaterial Ag or TDNA may affect the concentration of the biomaterial. The concentration of the biomaterial may be calculated by the changed amount of the resonant wavelength.

FIGS. 5A to 5D illustrate operations of the optical biosensor in FIG. 2.

Figure 5A:
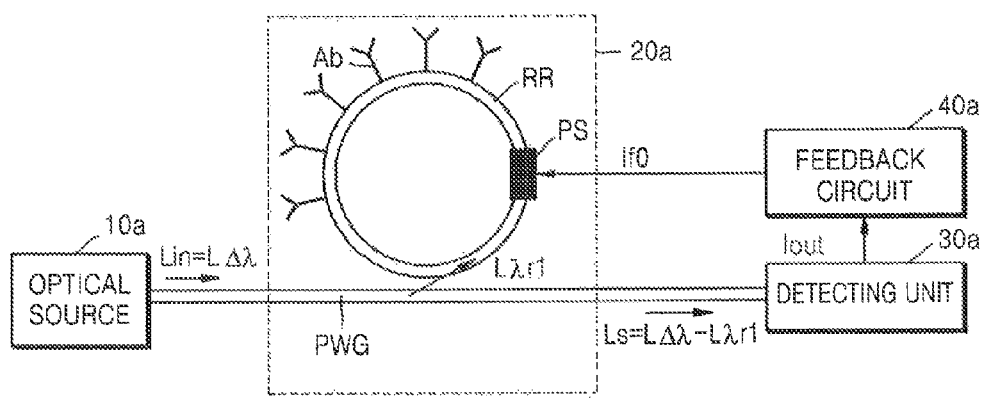
FIGS. 5A to 5D illustrate operations of the optical biosensor in FIG. 2.
Figure 5B:
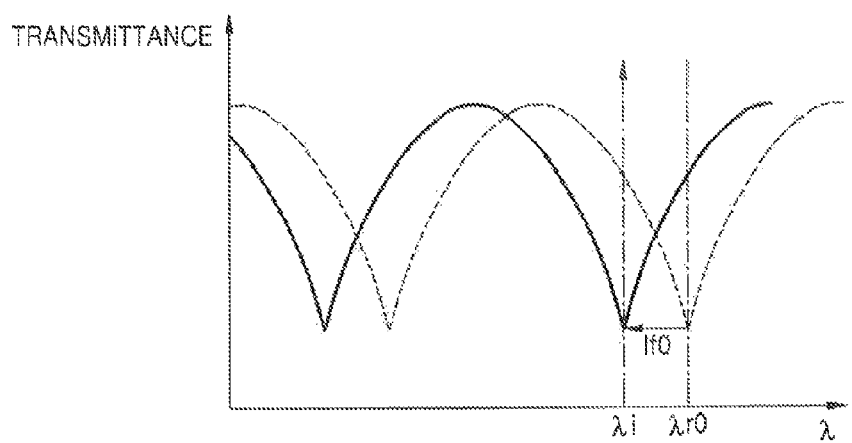
Figure 5C:
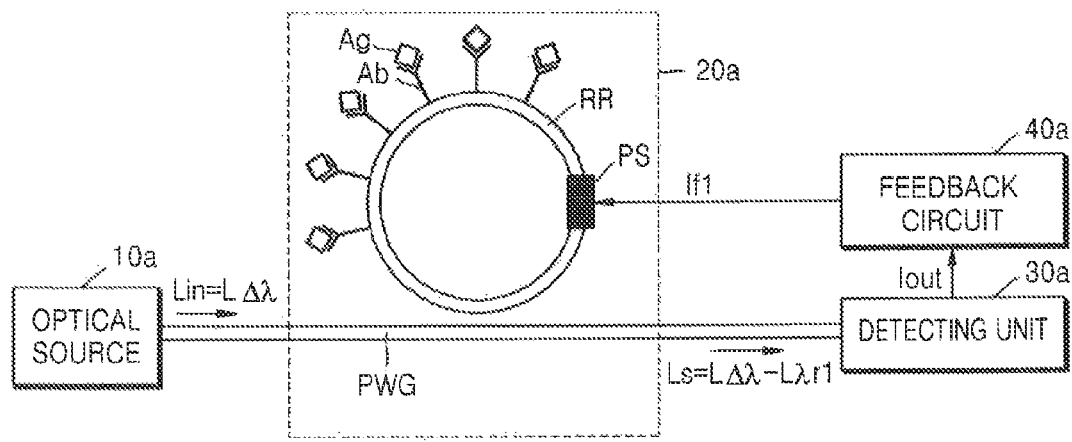
Figure 5D:
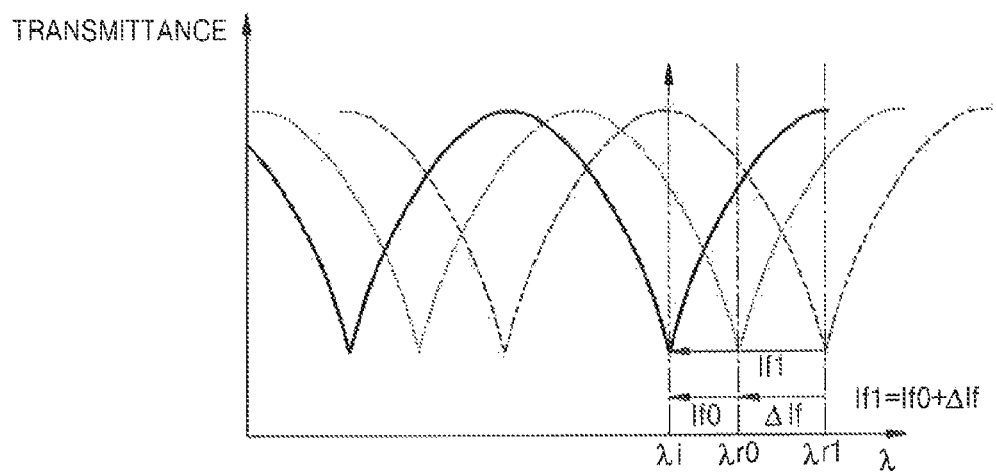

FIG. 5A illustrates an optical biosensor when a probe biomaterial is attached to a surface of the ring resonator RR. FIG. 5B illustrates an optical spectral transmittance of the ring resonator of FIG. 5A (see, for example, short dotted line). FIG. 5C illustrates when a target biomaterial is combined into the probe biomaterial. FIG. 5D illustrates an optical spectral transmittance of the ring resonator (see, for example, long dotted line).

Referring to FIGS. 5A and 5B, a probe biomaterial may be attached to a surface of the ring resonator RR. For example, the probe biomaterial may be an antibody Ab. A target biomaterial may flow into the biosensing unit 20a to combine with the probe biomaterial. The target biomaterial may be an antigen Ag. Hereinafter, a state where a probe biomaterial is attached to a surface of a ring resonator RR is referred to as a reference state. A state where a target biomaterial is combined into the probe biomaterial is referred to as a sensing state.

An optical spectral transmittance of the biosensing unit 20a may be lowest at the resonant wavelength of the ring resonator RR. The strength of the detection signal Iout may be a minimum when the optical spectral transmittance of the biosensing unit 20a is lowest at the wavelength of the input optical signal Lin. The reference feedback signal may control the resonant wavelength of the ring resonator RR to be same as the wavelength of the input optical signal Lin such that the optical spectral transmittance of the biosensing unit 20a may be lowest at the wavelength λi of the input optical signal Lin. As described above in relation to FIGS. 4A and 4B, resonant wavelengths of the ring resonator RR between the reference state and the sensing state differ from each other. The strength of the feedback signals applied to the phase shifter PS to control the resonant wavelength to be same as the wavelength of the input optical signal Lin may be different in the reference state and the sensing state. Referring to FIGS. 5A and 5B, a resonant wavelength of the ring resonator RR may be λr0 and an optical transmittance of the biosensing unit 20a may be lowest at λr0 before a feedback signal in the reference state (refer to as "reference feedback signal") is applied to the phase shifter PS. In the reference state, the reference feedback signal required to control the resonant wavelength to be same as the wavelength λi of the input optical signal Lin may be If0. The resonant wavelength of the ring resonator RR may be changed from the wavelength λr0 to the wavelength λi in response the reference feedback signal If0 such that the optical spectral transmittance of the biosensing unit 20a may be lowest at the wavelength λi of the input optical signal Lin. Referring to FIGS. 5C and 5D, the resonant wavelength of the ring resonator RR may be λr1 and an optical spectral transmittance of the biosensing unit 20a may be lowest at λr1 before a feedback signal in the sensing state (refer to as "sensing feedback signal") is applied to the phase shifter PS. The sensing feedback signal required to control the resonant wavelength to be same as the wavelength λi of the input optical signal Lin may be If1. The resonant wavelength of the ring resonator RR may be changed from the wavelength λr1 to the wavelength λi in response the reference feedback signal If1 such that the optical spectral transmittance of the biosensing unit 20a may be lowest at the wavelength λi of the input optical signal Lin. As shown in FIG. 5D, the resonant wavelength λr0 in the reference state may be closer to the wavelength λi of the input optical signal Lin than the resonant wavelength λr1 in the sensing state. The sensing feedback signal If1 in the sensing state may be larger than the reference feedback signal If0 in the reference state. The difference between the reference feedback signal If0 and the sensing feedback signal If1 may be ΔIf and proportional to the difference between the resonant wavelength in the reference state and the resonant wavelength in the sensing state. The changed amount of the resonant wavelength may be calculated from the difference between the reference feedback signal and the sensing feedback signal ΔIf.

Figure 6:
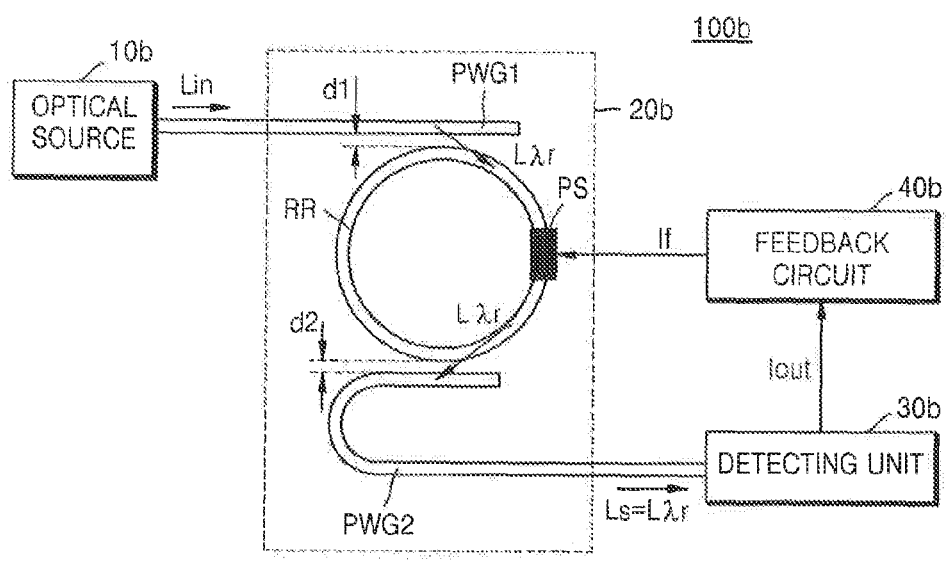
FIG. 6 illustrates an example of the optical biosensor of FIG. 1.

FIG. 6 illustrates an embodiment of the optical biosensor 100 in FIG. 1.

Referring to FIG. 6, the optical biosensor 100 may include an optical source 10b, a biosensing unit 20b, a detecting unit 30b, and a feedback circuit 40b. The optical source 10b, the detecting unit 30b, and the feedback circuit 40b may be same or similar to those in FIG. 2.

The biosensing unit 20b may include a first optical waveguide PWG1, a ring resonator RR, a phase shifter PS, and a second optical waveguide PWG2. Although not shown in the drawings, a fluidic channel may be disposed on top surfaces of the first optical waveguide PWG1, the ring resonator RR, and the second optical waveguide PWG2. A biomaterial flowed in through the fluidic channel may change the resonant wavelength of the ring resonator RR. The first and second optical waveguides PWG1 and PWG2 may be straight optical waveguides. The ring resonator RR may be an optical waveguide of a circular or racetrack form. A phase shifter PS may be disposed on a part of the ring resonator RR.

The ring resonator RR may be disposed apart from the first optical waveguide PWG1 with a first gap d1 interposed between the ring resonator RR and the first optical waveguide PWG1. The ring resonator RR may be disposed apart from the second optical waveguide PWG2 with a second gap d2 interposed between the ring resonator RR and the second optical waveguide PWG2. In an embodiment, the ring resonator RR may be disposed horizontally, for example on a common layer, with the first optical waveguide PWG1 with a first gap d1 interposed between the ring resonator RR and the first optical waveguide PWG1. The ring resonator RR may be disposed horizontally, for example on a common layer, with the second optical waveguide PWG2 with a second gap d2 interposed between the ring resonator RR and the second optical waveguide PWG2. In an embodiment, the ring resonator RR may be also disposed vertically, for example on a different layer, with the first optical waveguide PWG1 with a first gap d1 interposed between the ring resonator RR and the first optical waveguide PWG1. The ring resonator RR may be disposed vertically, for example on a different layer, with the second optical waveguide PWG2 with a second gap d2 interposed between the ring resonator RR and the second optical waveguide PWG2.

When an input optical signal Lin having a center wavelength $\lambda i$ is incident to the first optical waveguide PWG1, the input optical signal Lin may travel along the optical waveguide PWG1 and transit to the ring resonator RR having a resonant wavelength. The input optical signal Lin transited to the ring resonator may propagate through the ring resonator RR. The input optical signal Lin may encounter a resonance at the resonant wavelength. The resonant optical signal at the resonant wavelength may be transited to the second optical waveguide PWG2 to be output as the sensed optical signal Ls. The output optical signal from the second optical waveguide PWG2 may be a signal whose resonant wavelength component is dropped from the input optical signal Lin. The output optical signal from the second optical waveguide PWG2 may be a signal whose resonant wavelength component is extracted from the input optical signal Lin. The output optical signal from the second optical waveguide PWG2 is not limited thereto.

When an electrical signal is applied to the phase shifter PS, the resonant wavelength $\lambda r$ of the ring resonator RR may be changed. The phase shifter PS may operate in response to a feedback signal If generated from the feedback circuit 40b.

When the detecting unit 30b converts the sensed optical signal Ls into an electrical signal and outputs the electrical signal as a detection signal Iout, the feedback circuit 40b may output the feedback signal If based on the detection signal Iout. The feedback signal If may be a voltage signal or a current signal. The feedback signal If may change the resonant wavelength $\lambda r$ of the ring resonator RR. The feedback signal If may control the resonant wavelength $\lambda r$ to be the same as a wavelength $\lambda i$ of the input optical signal Lin. The sensed optical signal Ls may be an optical signal whose resonant wavelength component is extracted from the input optical signal Lin. The sensed optical signal Ls may be an optical signal whose resonant wavelength component is dropped from the input optical signal Lin. For example, when the sensed optical signal Ls is an optical signal whose resonant wavelength component is extracted from the input optical signal Lin, the strength of the detection signal Iout may be a maximum. The feedback circuit 40b may change and output a feedback signal If until the strength of the detection signal Iout becomes a maximum.

Figure 7:
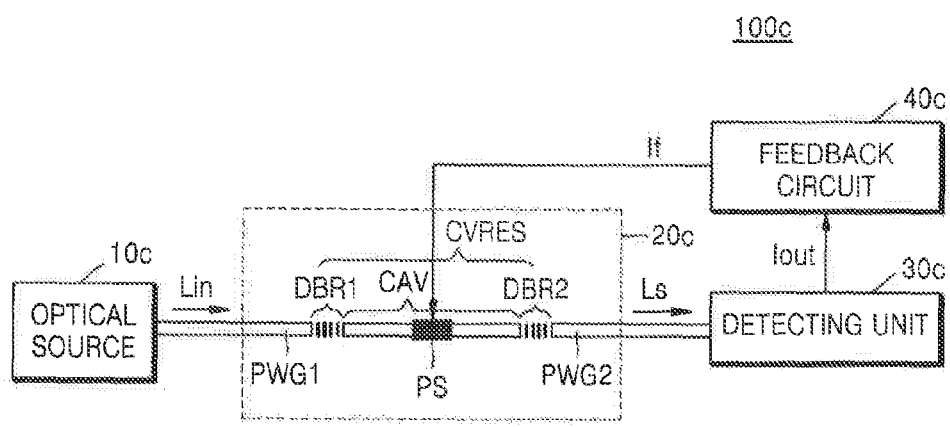
FIG. 7 illustrates an example of the optical biosensor of FIG. 1.

FIG. 7 illustrates an example of the optical biosensor 100 in FIG. 1.

Referring to FIG. 7, the optical biosensor 100 may include an optical source 10c, a biosensing unit 20c, a detecting unit 30c, and a feedback circuit 40c. The optical source 10c, a detecting unit 30c, and a feedback circuit 40c may be same or similar to those in FIG. 2.

The biosensing unit 20c may generate a sensed optical signal Ls. The sensed optical signal Ls may be an optical signal whose resonant wavelength component is extracted from an input optical signal Lin. The resonant wavelength of the biosensing unit 20c may be changed according to a concentration of the biomaterial attached to the biosensing unit 20c.

In the present embodiment, the biosensing unit 20c may include a first optical waveguide PWG1, a cavity resonator CVRES, a phase shifter PS, and a second optical waveguide PWG2. The cavity resonator CVRES may extract only the resonant wavelength from an input optical signal Lin to provide to the second optical waveguide PWG2 as a sensed optical signal Ls. The phase shifter PS may be disposed in a part of a cavity CAV. The resonant wavelength of the cavity CAV may be changed in response to an electrical signal applied to the phase shifter PS.

The cavity resonator CVRES may include two distributed Bragg reflectors DBR1 and DBR2, and the cavity CAV. The distributed Bragg reflectors DBR1 and DBR2 may reflect a specific wavelength from among wavelengths of the input optical signal Lin. The two distributed Bragg reflectors DBR1 and DBR2, and the cavity CAV may be combined to operate as a resonator. A sensed optical signal Ls outputted through the second optical waveguide PWG2 may be a signal whose resonant wavelength component is extracted from the input optical signal Lin.

A probe biomaterial may be attached to a top surface of the cavity CAV, and then a target biomaterial may be combined into the probe biomaterial. When the target biomaterial is combined into the probe biomaterial, an effective refractive index of the cavity resonator CVRES may be changed according to a combination degree between the probe material and the target material. The combination degree may be proportional to the concentration of the target biomaterial. A resonant wavelength may be changed as the effective refractive is changed. The resonant wavelength may be changed as the concentration of the target biomaterial is changed.

The detecting unit 30c may convert the sensed optical signal Ls to an electrical signal and output the electrical signal as a detection signal Iout. The detection signal Iout may be a voltage or a current signal. The feedback circuit 40c may output a feedback signal If based on the detection signal Iout. The feedback signal If may be applied to the phase shifter PS to change the resonant wavelength of the cavity resonator CVRES to be same as the wavelength of the input optical signal Lin. An operation of the optical biosensor 10c, not described herein, may be the same or similar to that in FIG. 2.

Figure 8:
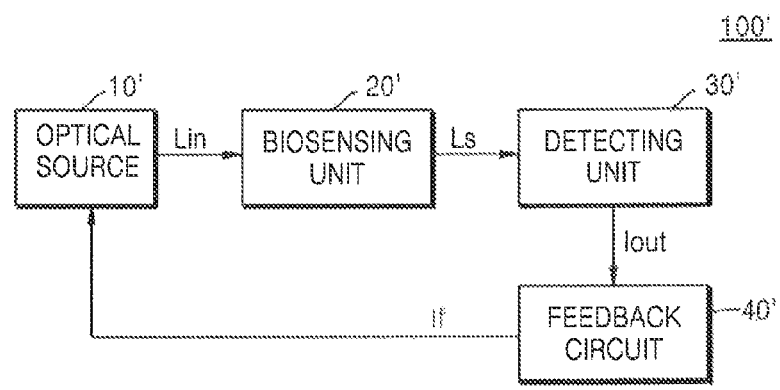
FIG. 8 is a block diagram illustrating an optical biosensor according to an embodiment of the present inventive concept.

FIG. 8 is a block diagram illustrating an optical biosensor according to an embodiment of the present inventive concept. Referring to FIG. 8, the optical biosensor 100' may include an optical source 10', a biosensing unit 20', a detecting unit 30', and a feedback circuit 40'.

The optical source 10' may generate an input optical signal Lin, and provide the generated input optical signal Lin to the biosensing unit 20'. The biosensing unit 20' may receive the input optical signal Lin and generate a sensed optical signal Ls. The sensed optical signal Ls may be an optical signal whose resonant wavelength component is extracted from an input optical signal Lin. The resonant wavelength of the biosensing unit 20' may be changed according to a concentration of the biomaterial. The resonant wavelength of the biosensing unit 20' may be changed according to the concentration of the biomaterial attached to the biosensing unit 20'.

The detecting unit 30' may receive the sensed optical signal Ls and convert the sensed optical signal Ls into an electrical signal and output the electrical signal as a detection signal Iout.

The feedback circuit 40' may output a feedback signal If. The feedback signal If may change the wavelength of the input optical signal Lin based on the detection signal Iout. The wavelength of the sensed optical signal Ls may be changed as the wavelength of the input optical signal Lin is changed. The feedback signal If is transmitted to the optical source 10'. The wavelengths of the input optical signal and the wavelength of the sensed optical signal Ls may be changed in response to the feedback signal If.

The feedback signal If may control the wavelength of the input optical signal Lin to be the same as the resonant wavelength of the biosensing unit 20'. The optical source 10' may generate and output an input optical signal whose wavelength is the same as the resonant wavelength of the biosensing unit 20'. When the wavelength of the input optical signal Lin and the resonant wavelength of the biosensing unit 20' are equal, the strength of the detection signal Iout may become a minimum or a maximum. The feedback circuit 40' may monitor the change of the detection signal Iout according to the change of the feedback signal If and output the feedback signal If to the optical source 10'. The feedback signal If may change the wavelength of the optical source 10' to adjust the strength of the detection signal Iout to be a minimum or a maximum.

The optical biosensor 100' may measure the feedback signal If and analyze the changed amount of the resonant wavelength. The wavelength of the input optical signal Lin may be controlled to be the same as the resonant wavelength of the biosensing unit 20' by the feedback signal If generated from the feedback circuit 40'. The feedback signal If may be changed as the resonant wavelength is changed. The resonant wavelength may be changed as the concentration of the biomaterial attached to the biosensing unit. A reference feedback signal may be measured in a reference state when a probe biomaterial is attached to the biosensing unit 20'. A sensing feedback signal may be measured in a sensing state when a target biomaterial is combined into the probe biomaterial. The changed amount of the resonant wavelength may be determined by the difference between the reference feedback signal and the sensing feedback signal. The concentration of the target biomaterial may be calculated based on the changed amount of the resonant wavelength.

Figure 9:
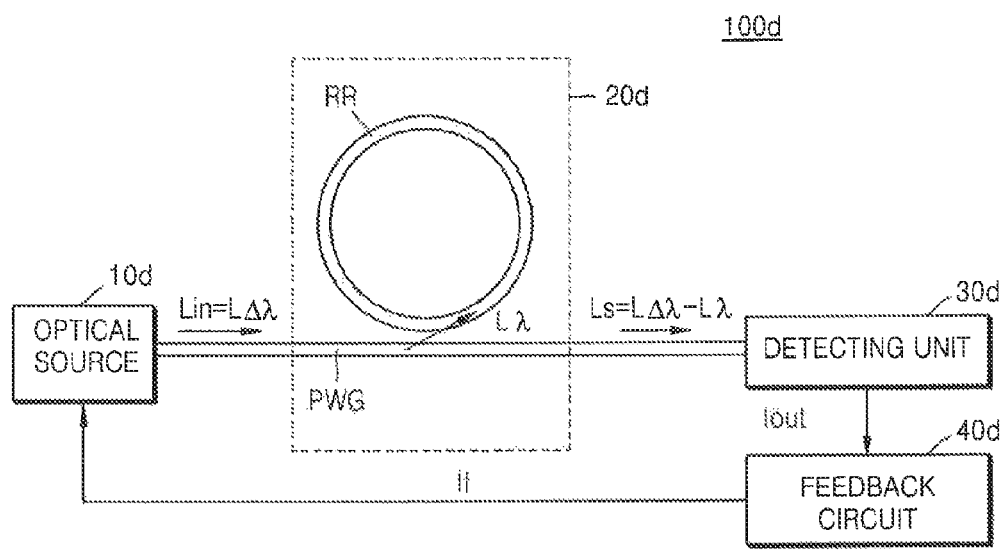
FIG. 9 illustrates an example of the optical biosensor of FIG. 8.

FIG. 9 illustrates an example of the optical biosensor 100d in FIG. 8.

Referring FIG. 9, the optical biosensor 100d may include an optical source 10d, a biosensing unit 20d, a detecting unit 30d, and a feedback circuit 40d. A configuration of the optical biosensor 100d may be the same or similar to the optical biosensor 100a in FIG. 2, except that a feedback signal from the feedback circuit 40d is transmitted to an optical source 10d.

The feedback circuit 40a in the optical biosensor 100a in FIG. 2 may generate a feedback signal to control a resonant wavelength of the ring resonator RR to be the same as the wavelength of the input optical signal Lin by a feedback signal If applied to the phase shifter PS. However, the feedback circuit 40d in the optical biosensor 100d of FIG. 9 may generate a feedback signal to control the optical source 10d to have the wavelength of the input optical signal Lin to be the same as the resonant wavelength λr.

FIGS. 10A to 10D illustrate operations of the optical biosensor 100d in FIG. 9.

Figure 10A:
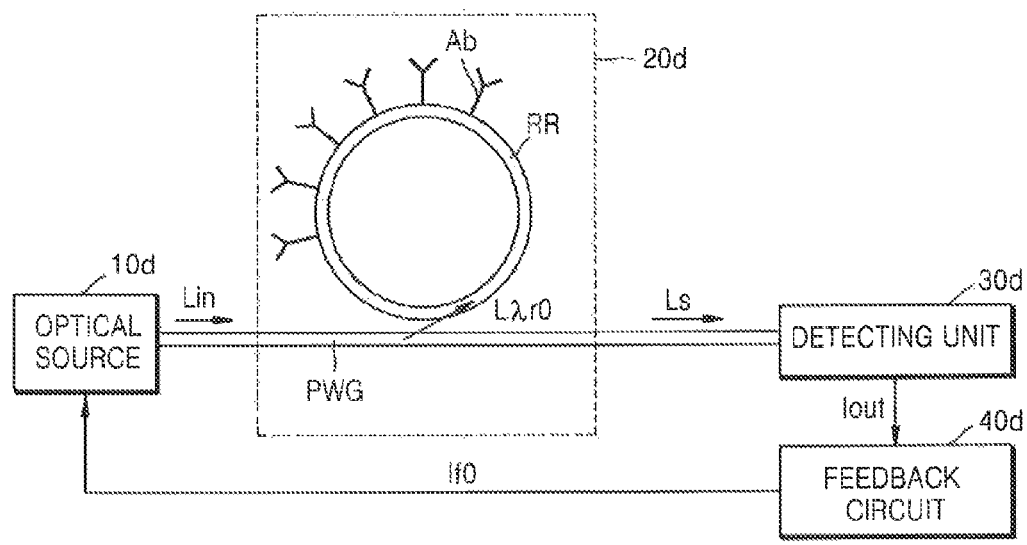
FIGS. 10A to 10D illustrate operations of the optical biosensor in FIG. 9.
Figure 10B:
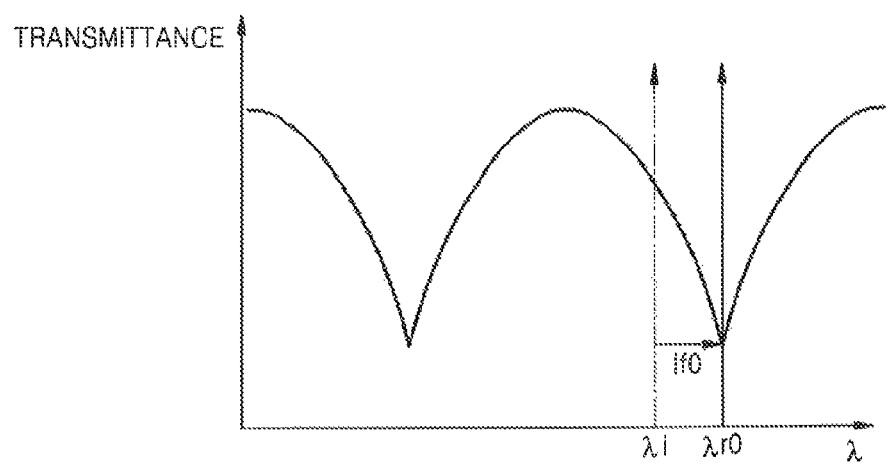
Figure 10C:
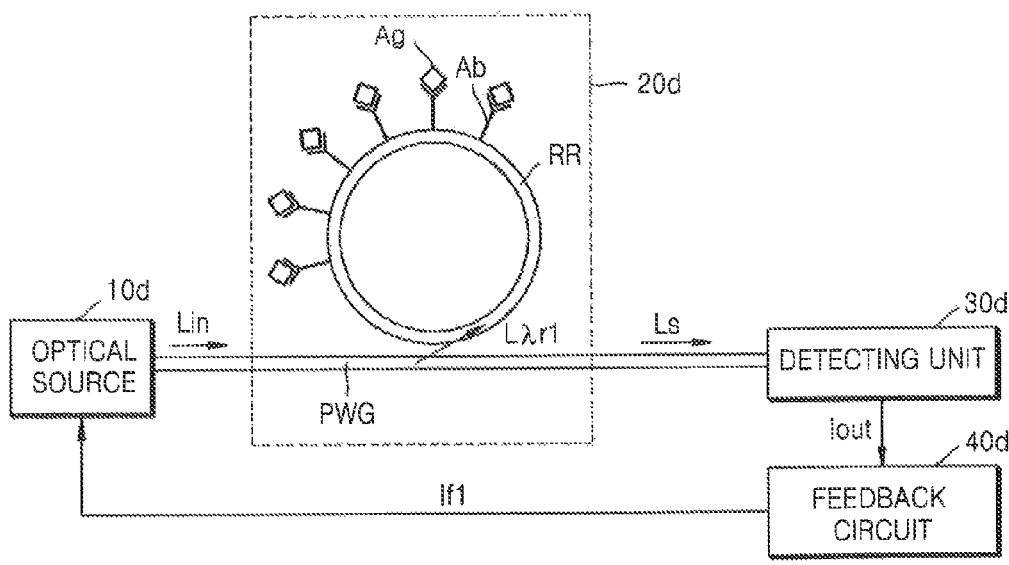
Figure 10D:
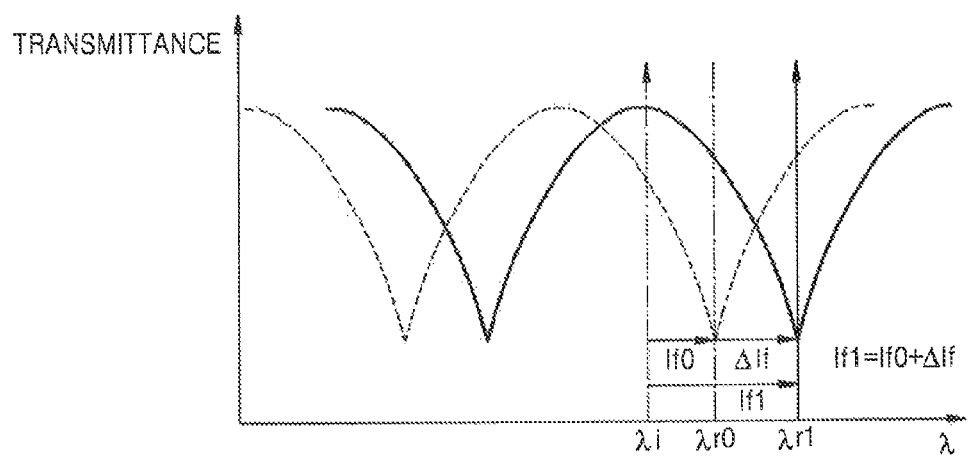

FIG. 10A illustrates an optical biosensor 20d when a probe biomaterial is attached to a surface of the ring resonator RR. FIG. 10B illustrates an optical spectral transmittance of FIG. 10A. FIG. 10C illustrates the optical biosensor 20d when a target biomaterial is combined into the probe biomaterial of FIG. 10C. FIG. 10D illustrates an optical spectral transmittance of the ring resonator of FIG. 10C. For example, the probe biomaterial may be an antibody Ab and the target biomaterial may be an antigen Ag.

The strength of the detection signal Iout may be a minimum when the light transmittance of the biosensing unit 20d is lowest at the wavelength of the input optical signal Lin. The reference feedback signal may control the wavelength of the input optical signal Lin to be same as the resonant wavelength of the ring resonator RR such that the optical spectral transmittance of the biosensing unit 20d may be lowest at the changed wavelength of the input optical signal Lin.

When the target biomaterial is combined into the probe biomaterial, an effective refractive index of the ring resonator RR may be changed. The effective refractive index of the ring resonator RR may change to vary the resonant wavelength of the ring resonator RR. The resonant wavelength may be different in the reference state and the sensing state.

A feedback signal required to control the wavelength of the input optical signal Lin to be the same as the resonant wavelength of the ring resonator RR may be different in the reference state and the sensing state. Referring to FIGS. 10A and 10B, the resonant wavelength in the reference state may be λr0 and an optical spectral transmittance of the biosensing unit 20d may be lowest at λr0 before a feedback signal in the reference state (refer to as "reference feedback signal") is applied to the phase shifter PS. In the reference state, a reference feedback signal required to control the wavelength of λi of the input optical signal Lin to be the same as the resonant wavelength λr0 may be If0. The wavelength of the input optical signal Lin may be changed from the wavelength λi to the wavelength λr0 in response the reference feedback signal If0 such that the wavelength of the input optical signal Lin may be the same as the wavelength λr0 at which the optical spectral transmittance of the biosensing unit 20d is lowest. Referring to FIGS. 10C and 10D, the resonant wavelength in the sensing state may be λr1 and an optical spectral transmittance of the biosensing unit 20d may be lowest at λr1 before a feedback signal in the sensing state (refer to as "sensing feedback signal") is applied to the phase shifter PS. In the reference state, a sensing feedback signal required to control the wavelength of λi of the input optical signal Lin to be the same as the resonant wavelength λr1 may be If1. The wavelength of the input optical signal Lin may be changed from the wavelength λi to the wavelength λr1 in response the reference feedback signal If1 such that the wavelength of the input optical signal Lin may be the same as the wavelength λr1 at which the optical spectral transmittance of the biosensing unit 20d is lowest. As shown in FIG. 10D, the difference between the reference feedback signal If0 and the sensing feedback signal If1 may be ΔIf. The changed amount of the resonant wavelength (λr1−λr0) may be determined by the feedback signal difference ΔIf.

Figure 11:
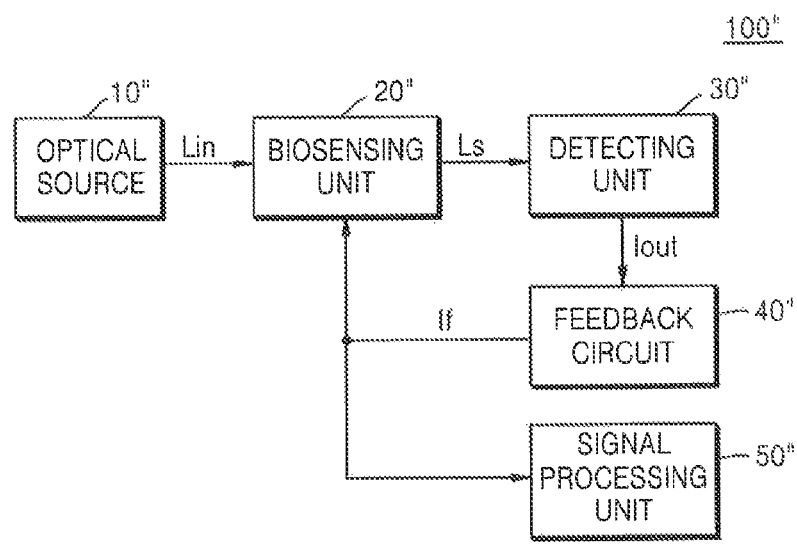
FIG. 11 is a block diagram of an optical biosensor according to an embodiment of the present inventive concept.

FIG. 11 is a block diagram of an optical biosensor according to an embodiment of the present inventive concept.

Referring to FIG. 11, the optical biosensor 100" may include an optical source 10", a biosensing unit 20", a detecting unit 30", a feedback circuit 40", and a signal processing unit 50". The optical source 10", the biosensing unit 20", the detecting unit 30", the feedback circuit 40", and the signal processing unit 50" may be formed on a semiconductor substrate. The optical source 10", the biosensing unit 20", the detecting unit 30", the feedback circuit 40", and the signal processing unit 50" may be integrated into one chip on a semiconductor substrate.

The optical biosensor 100" may further include a signal processing unit 50". The optical source 10", the biosensing unit 20", the detecting unit 30", and the feedback circuit 40" may be the same or similar to, respectively, the optical source 10, the biosensing unit 20, the detecting unit 30, and the feedback circuit 40 in FIG. 1. Detailed description of the optical source 10", the biosensing unit 20", the detecting unit 30", and the feedback circuit 40" is omitted.

The signal processing unit 50" may calculate changed amount of the resonant wavelength of the bio sensing unit 20" based on the difference between a reference feedback signal and a sensing feedback signal. The signal processing unit 50" may calculate concentration of a target biomaterial by using the changed amount of the resonant wavelength of the bio sensing unit 20". The reference feedback signal may be generated by the feedback circuit 40" when a probe biomaterial is attached to the biosensing unit 20". The sensing feedback signal may be generated by the feedback circuit 40" when a target biomaterial is combined into the probe biomaterial. The concentration of the target biomaterial combined into the probe biomaterial may affect the strength of the sensing feedback signal and the changed amount of the resonant wavelength in the biosensing unit 20". For a biomaterial, the signal processing unit 50" may store, in advance, a data about changed amount of the resonant wavelength in the sensing biosensing unit 20" varying according to the concentration of the target biomaterial. The concentration of the target biomaterial may be calculated by the corresponding changed amount of the resonant wavelength in the biosensing unit 20". However, algorithm or method for calculating concentration of a target biomaterial is not limited thereto.

Figure 12:
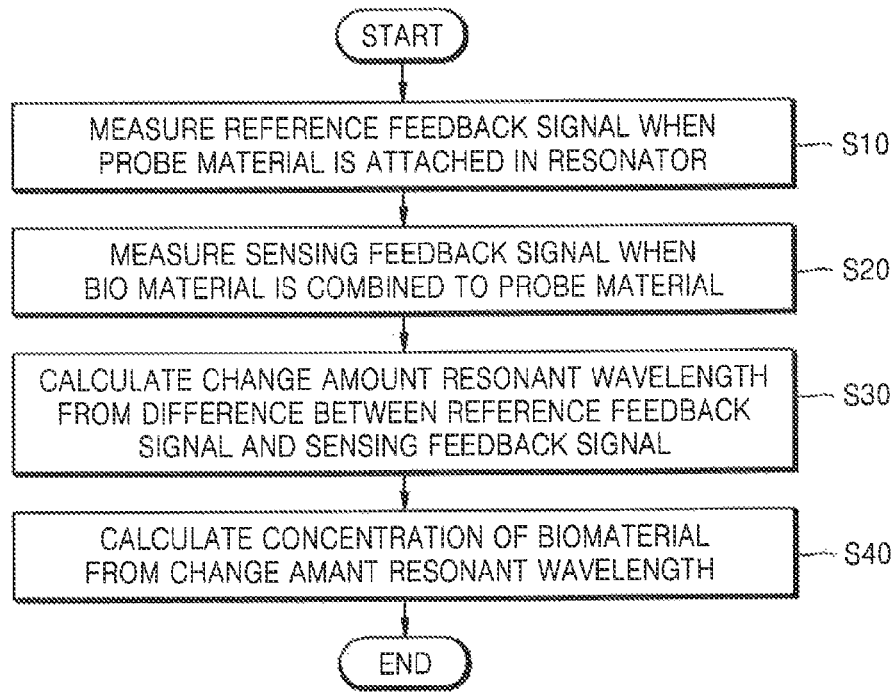
FIG. 12 is a flow chart illustrating a method of calculating concentration of a biomaterial according to an embodiment of the present inventive concept.

FIG. 12 illustrates a method of calculating concentration of a target biomaterial according to an embodiment of the present inventive concept.

The concentration of the target biomaterial may be calculated by using any of the optical biosensors 100, 100', or 100" described above.

Referring to FIG. 12, a reference feedback signal may be measured of an optical biosensor when a probe biomaterial is attached to a resonator in a biosensing unit (operation S10). The optical biosensor may include the feedback circuit (for example, 40 in FIG. 1) and the feedback circuit may output a feedback signal based on a detection signal. The feedback signal may be transmitted to either the resonator in the biosensing unit or an optical source in order to have the resonant wavelength of the resonator and the wavelength of an input optical signal to be equal. When the resonant wavelength and the wavelength of the optical source become equal, the detection signal may be a minimum or a maximum and the feedback signal at the output of the feedback circuit may be measured as a reference feedback signal.

A sensing feedback signal may be measured of the optical biosensor when the target biomaterial is combined into the probe biomaterial (operation S20). When the resonant wavelength and the wavelength of the optical source are the same, the detection signal may be a minimum or a maximum and the feedback signal at the output of the feedback circuit may be measured as a sensing feedback signal.

The changed amount of the resonant wavelength may be calculated from the difference between the measured reference feedback signal and the sensing feedback signal (operation S30). The difference between the measured reference feedback signal and the sensing feedback signal may be proportional to the changed amount of the resonant wavelength.

The concentration of the target biomaterial may be calculated from the changed amount of the resonant wavelength (operation S40). The changed amount of resonant wavelength varying according to concentration of a biomaterial may be stored as a data in advance. The concentration of the target biomaterial may be calculated by the corresponding changed amount of the resonant wavelength.

Figure 13:
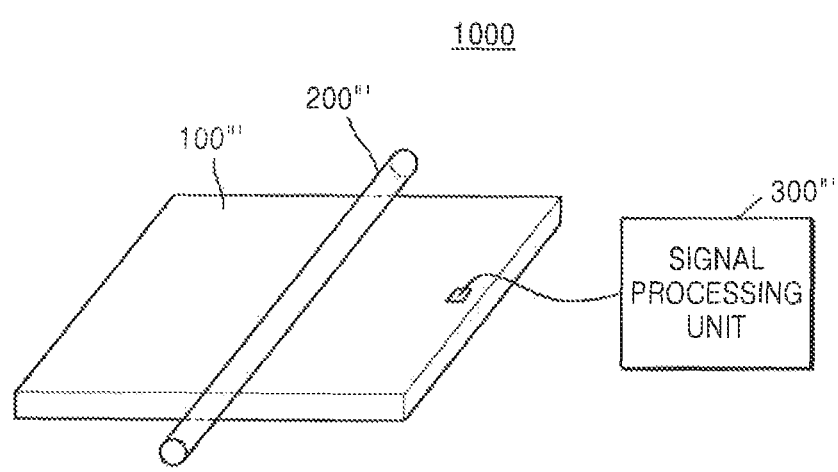
FIG. 13 is a block diagram illustrating a biosensing system according to an embodiment of the present inventive concept.

FIG. 13 is a block diagram illustrating a biosensing system according to an embodiment of the present inventive concept.

Referring to FIG. 13, the biosensing system 1000 may include a biosensor chip 100''', a fluidic channel 200''', and a signal processing unit 300'''.

The biosensor chip 100''' may sense concentration of a target biomaterial by using optical characteristics and output a sensed concentration as an electrical signal. The biosensor chip 100''' may be the optical biosensor 100, 100', or 100" with reference to FIGS. 1, 8, and 11. For example, a biosensing unit 20, 20', or 20", a detecting unit 30, 30', or 30", and a feedback circuit 40, 40', or 40" may be integrated into the biosensor chip 100'''. For example, an optical source 10, 10', or 10" may be integrated into the biosensor chip 100'''. The biosensor chip 10''' might not need an external optical source or a spectrometer and may be miniaturized.

The fluidic channel 200''' may be a passage through which a biomaterial flows. The fluidic channel 200''' may be arranged on a top surface of the biosensor chip 100'''. The fluidic channel 200''' may be arranged on a portion where the biosensing unit is located. When a fluid or a gas including a biomaterial flows through the fluidic channel 200''', the biomaterial may contact the biosensor chip 100'''. The fluidic channel 200''' may be a micro fluidic channel or may be formed on a micro fluidic chip. In the drawing, although the fluidic channel 200''' is shown as a straight line type, however the fluidic channel 200''' is not limited thereto.

The signal processing unit 300''' may measure concentration of a biomaterial by calculating change amount of the resonant wavelength of the biosensor chip 100'''. The electrical signal output from the biosensor chip 100''' may include a signal of the change amount of the resonant wavelength of the biosensor chip 100'''. The change amount of the resonant wavelength of the biosensor chip 10''' may be calculated by the difference between the feedback signal generated when the probe biomaterial is attached to the biosensor chip 100''' and the feedback signal generated when the target biomaterial is combined into the probe biomaterial. For example, the signal processing unit 300''' may be located in an electronic processing system such as a computer. The signal processing unit 300''' may obtain the electrical signal through a connection terminal and a connection code (not shown). The signal processing unit 300''' may be embedded in an independent biosensor system with the biosensor chip 100''' and the fluidic channel 200'''.

While the inventive concept has been particularly shown and described with reference to exemplary embodiments thereof, it will be understood that various changes in form and details may be made therein without departing from the spirit and scope of the following claims.

What is claimed is:

1. An optical biosensor, comprising:
    a biosensing unit configured to receive an input optical signal, sense a target biomaterial, and generate a sensed optical signal;
    a detecting unit configured to convert the sensed optical signal into an electrical signal and output the electrical signal as a detection signal; and
    a feedback circuit configured to output a feedback signal generated based on the detection signal, wherein the feedback signal is changed based on change in a resonant wavelength of the biosensing unit.

2. The optical biosensor of claim 1, wherein the feedback circuit controls the resonant wavelength of the biosensing unit to be equal to a wavelength of the input optical signal by using the feedback signal.

3. The optical biosensor of claim 1, wherein the feedback circuit controls a wavelength of the input optical signal to be equal to the resonant wavelength of the biosensing unit by using the feedback signal.

4. The optical biosensor of claim 1, wherein the feedback signal is a voltage signal or a current signal.

5. The optical biosensor of claim 1, further comprising an optical source providing the input optical signal.

6. The optical biosensor of claim 1, wherein the biosensing unit, the detecting unit, and the feedback circuit are formed on a same substrate.

7. The optical biosensor of claim 1, further comprising a signal processing unit calculating a concentration of the target biomaterial by calculating a difference between a reference feedback signal generated when a probe biomaterial is attached to the biosensing unit and a sensing feedback signal generated when the target biomaterial is combined into the probe biomaterial.

8. The optical biosensor of claim 2, wherein the biosensing unit comprises:
    a resonator configured to provide the resonant wavelength and to output the sensed optical signal; and
        a phase shifter configured to receive the feedback signal and change the resonant wavelength of the resonator in response to the feedback signal.

9. The optical biosensor of claim 2, where the biosensing unit comprises:
    an optical waveguide configured to receive the input optical signal;
    a ring resonator configured to provide the resonant wavelength and to output the sensed optical signal through a gap interposed between the optical waveguide and the ring resonator; and
    a phase shifter configured to change the resonant wavelength of the ring resonator in response to the feedback signal.

10. The optical biosensor of claim 2, wherein the biosensing unit comprises:
    a first optical waveguide configured to receive the input optical signal;
    a ring resonator configured to provide the resonant wavelength and to output the sensed optical signal through a gap interposed between the first optical waveguide and the ring resonator;
    a phase shifter configured to change the resonant wavelength of the ring resonator in response to the feedback signal; and
    a second optical waveguide configured to output the sensed optical signal through a gap interposed between the ring resonator and the second optical waveguide.

11. The optical biosensor of claim 2, wherein the biosensing unit comprises:
    a first optical waveguide configured to receive the input optical signal;
    a cavity resonator configured to provide the resonant wavelength and to output the sensed optical signal;
    a second optical waveguide configured to receive the sensed optical signal; and
    a phase shifter configured to change the resonant wavelength of the cavity resonator.

12. The optical biosensor of claim 11, wherein the cavity resonator includes a Bragg reflector.

13. The optical biosensor of claim 5, wherein the optical source is configured to change the wavelength of the input optical signal in response to the feedback signal.

14. A biosensing system, comprising:
    a biosensor chip configured to sense a target biomaterial based on an input optical signal, and output a feedback signal; and
    a signal processing unit configured to analyze the feedback signal and calculate a concentration of the target biomaterial,
    wherein the biosensor chip comprises:
        a biosensing unit configured to receive the input optical signal, sense the target biomaterial, and generate a sensed optical signal;
        a detecting unit configured to convert the sensed optical signal into an electrical signal and output the electrical signal as a detection signal; and
        a feedback circuit configured to output the feedback signal generated based on the detection signal,
            wherein the feedback circuit controls a resonant wavelength of the biosensing unit to be equal to a wavelength of the input optical signal by using the feedback signal.

15. The biosensing system of claim 14, wherein the biosensing unit comprises a resonator configured to provide the resonant wavelength and to output the sensed optical signal, wherein the signal processing unit calculates the concentration of the target biomaterial by calculating a difference between a reference feedback signal generated when a probe biomaterial is attached to the biosensing unit and a sensing feedback signal generated when the target biomaterial is combined into the probe biomaterial.

16. The biosensing system of claim 14, wherein the biosensing system further comprises an optical source configured to generate the input optical signal, wherein the optical source is integrated on the substrate which the biosensor chip is formed.

17. A biosensing system comprising:
    a biosensor chip configured to sense a target biomaterial based on an input optical signal, and output a feedback signal; and
    a signal processing unit configured to analyze the feedback signal and calculate a concentration of the target biomaterial,
    wherein the biosensor chip comprises:
        a biosensing unit configured to receive the input optical signal, sense the target biomaterial, and generate a sensed optical signal;
        a detecting unit configured to convert the sensed optical signal into an electrical signal and output the electrical signal as a detection signal; and
        a feedback circuit configured to output the feedback signal generated based on the detection signal, wherein the feedback circuit controls a wavelength of the input optical signal to be equal to a resonant wavelength of the biosensing unit by using the feedback signal.

* * * * *